United States Patent
George et al.

(10) Patent No.: US 9,810,685 B2
(45) Date of Patent: Nov. 7, 2017

(54) HIGH-THROUGHPUT PLATFORM COMPRISING MICROTISSUES PERFUSED WITH LIVING MICROVESSELS

(75) Inventors: Steven C. George, Irvine, CA (US); Christopher C. W. Hughes, Irvine, CA (US); Abraham P. Lee, Irvine, CA (US); Monica Moya, Irvine, CA (US); Yu-Hsiang Hsu, Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/253,820

(22) Filed: Oct. 5, 2011

(65) Prior Publication Data

US 2012/0083425 A1    Apr. 5, 2012

Related U.S. Application Data

(60) Provisional application No. 61/404,619, filed on Oct. 5, 2010.

(51) Int. Cl.
*G01N 33/50* (2006.01)
*C12N 5/00* (2006.01)
*C12N 5/071* (2010.01)

(52) U.S. Cl.
CPC ....... *G01N 33/5082* (2013.01); *C12N 5/0062* (2013.01); *C12N 5/0691* (2013.01); *G01N 33/5008* (2013.01); *G01N 33/5011* (2013.01); *C12N 2533/30* (2013.01); *C12N 2535/00* (2013.01)

(58) Field of Classification Search
CPC ...... C12M 23/16; C12M 29/10; C12M 21/08; B01L 9/527; A01N 1/0247; A01N 1/021; A01N 1/02; B81B 2201/058
USPC .......................................................... 435/325
See application file for complete search history.

(56) References Cited

U.S. PATENT DOCUMENTS 6,197,575 B1 *   3/2001   Griffith ................ B01J 19/0046
                                                                435/288.4
2006/0173394 A1 *   8/2006   Stroock et al. ................. 602/41

OTHER PUBLICATIONS

Chen et al. Prevascularization of a fibrin-based tissue construct accelerates the formation of functional anastomosis with host vasculature. Tissue Engineering. 2009;15(6):1363-1371.*

Swartz et al. Interstitial flow and its effects in soft tissues. Annu. Rev. Biomed. Eng. 2007;9:229-256.*
Borenstein J, Teraj H, King K, Weinberg E, Kaazempur-Mofrad M, and Vacanti J. Microfabrication technology for vascularized tissue engineering. Biomed Microdevices 4: 167-175, 2002.
Chen X, Aledia AS, Ghajar CM, Griffith CK, Putnam AJ, Hughes CWC, and George SC. Prevascularizing an engineered tissue construct accelerates formation of functional anastomosis with host vasculature. Tissue Eng (in press) 2008.
Chrobak KM, Potter DR, and Tien J. Formation of perfused, functional microvascular tubes in vitro. Microvasc Res 71: 185-196, 2006.
Ghajar CM, Chen X, Harris JW, Suresh V, Hughes CC, Jeon NL, Putnam AJ, and George SC. The effect of matrix density on the regulation of 3-D capillary morphogenesis Biophys J 94: 1930-1941, 2008.
Griffith CK, Miller C, Sainson RC, Calvert JW, Jeon NL, Hughes CC, and George SC. Diffusion limits of an in vitro thick prevascularized tissue. Tissue Eng 11: 257-266, 2005.
Helm CL, Fleury ME, Zisch AH, Boschetti F, and Swartz MA. Synergy between interstitial flow and VEGF directs capillary morphogenesis in vitro through a gradient amplification mechanism. Proc Nati Acad Sci U S A 102: 15779-15784, 2005.
Helm CL, Zisch A, and Swartz MA. Engineered blood and lymphatic capillaries in 3-D VEGF-fibrin-collagen matrices with interstitial flow. Biotechnol Bioeng 96: 167-176, 2007.
Ng CP, Helm CL, and Swartz MA. Interstitial flow differentially stimulates blood and lymphatic endothelial cell morphogenesis in vitro. Microvasc Res 68: 258-264, 2004.
Shin M, Matsuda K, Ishii O, Terai H, Kaazempur-Mofrad M, Borenstein J, Detmar M, and Vacanti JP. Endothelialized networks with a vascular geometry in microfabicated poly(dimethyl siloxane). Biomed Microdevices 6: 269-278, 2004.

* cited by examiner

*Primary Examiner* — Lynn Y Fan
(74) *Attorney, Agent, or Firm* — Berliner & Associates (57) ABSTRACT

Provided is a process for creating a 3D metabolically active microtissue perfused with living microvessels which have a direct fluidic connection with neighboring microfluidic channels. The process comprises preparing a template comprising a plurality of channels, and creating a network within said channels, said network comprising microfluidic channels, metabolically active living microvessels, and microtissues. The microvessels can sprout from said microvessels and/or form within the microtissue in response to a stimulus applied from said microfluidic channels or stimulus derived from the said tissues. In another embodiment, a device is provided comprising a supportive structure, one or more microfluidic channels, one or more microtissue compartments, and one or more microvessels, whereby the microvessels connect said microfludic channels and microtissue and perfuse the microtissue to deliver fluid from the microfluidic channels to the microtissues.

25 Claims, 8 Drawing Sheets

Table 1. Design Variables [#]

| Variable | Description | Range |
|---|---|---|
| $L_i$ | Length of channel | 1-10 cm |
| $W_i$ | Width of channel | 5-100 μm |
| $H_i$ | Height of channel | 5-100 μm |
| $L_t$ | Length of tissue | 100-1000 μm |
| $W_t$ | Width of tissue | 500-1000 μm |
| $Q_a$ | Flow in arteriole | * |
| $Q_v$ | Flow in venule | * |
| $\gamma$ | Shear rate at endothelial | 50-200 s$^{-1}$ [§] |
| $\rho_m$ | Density of extracellular | 2.5-10 mg/ml |
| $\rho_{str}$ | Density of stromal cells | $10^3$-$10^5$ |
| $d_p$ | size of "vessel" pores | 3-5 μm |
| $z_p$ | Spacing between pores | 5-10 μm |
| $n_p$ | Number of pores (per | 6-120 |
| z | Spacing between "tissues" | 100-500 μm |
| $d_l$ | Size of "lymph" pores | 5-20 μm |
| $\rho_l$ | Density of "lymph" pores | |
| $P_a$ | arteriole hydrostatic | 20-30 mmHg |
| $P_v$ | venule hydrostatic pressure | 2-5 mmHg |
| $P_{a,O2}$ | Inlet capillary oxygen | 20-100 |

[#] additional variables include endothelial cell type, stromal cell type, fluid and matrix composition (e.g., growth factors can be added or subtracted, and matrix can be collagen or fibrin).
\* Range will be determined by dimensions of the channel to achieve desired wall shear rate, $\gamma$.
[§] based on in-vivo range for small arterioles.
[¶] based on successful range for non-perfused capillary growth in fibrin.

Figure 3 A, B and C.

A) Low Longitudinal Flow

B) High Longitudinal Flow

C) High Radial Flow

HIGH-THROUGHPUT PLATFORM COMPRISING MICROTISSUES PERFUSED WITH LIVING MICROVESSELS

CROSS REFERENCE TO RELATED APPLICATIONS

This application claims the benefit of Provisional Patent Application No. 61/404,619, filed on Oct. 5, 2010, which is incorporated by reference herein in its entirety.

GOVERNMENT FUNDING/SUPPORT

This invention was made with Government support with a grant from the National Institutes of Health (RC1-ES018361). The Government has certain rights in this invention.

FIELD OF THE INVENTION

The invention relates to the creation of in vitro microtissues; more particularly microtissues constructed on a microfabricated platform and perfused with living microvessels.

BACKGROUND OF THE INVENTION

The challenge to create the microenvironment enabling growth of an in-vitro microtissue perfused with living microvessels (e.g., arterioles, capillaries, and venules) represents a completely new paradigm in the creation of 3-D tissues. By definition, a 3-D tissue requires enhanced transport of nutrients and waste relative to 2-D monolayer cultures. Current approaches to create such an environment have employed three primary approaches: 1) enhanced concentration gradients of nutrients and waste while relying on molecular diffusion (Brownian motion) as the mode of transport, 2) the creation of microchannels in the tissue to enhance advection (forced convection), or 3) forced interstitial fluid flow. In-vivo, diffusion of nutrients and waste is the mechanism of transport once solutes exit the capillary bed, and is generally limited to distances <250 μm. The rate of transport is proportional to the concentration difference between two points, and inversely related to the separation distance. Hence, numerous 3-D tissue models have been reported with dimensions on the order of 1-10 mm by simply enhancing the oxygen tension (room air is 160 mmHg compared to 20-30 mmHg in the interstitial tissue) and concentration of other nutrients (e.g., glucose).

More recently, microfabrication technology has led to the creation of precise microchannels on non-biological substrates (e.g., silicon or polydimethyl siloxane, PDMS)[1, 2] or within biological substrates such as collagen[3]. While these approaches offer the distinct advantage of introducing advection as a mechanism of transport, even when "endothelialized", the channels are not living microvessels. Hence, while this approach may assist the creation of larger engineered tissues, they are of less benefit in understanding in vivo biological functions such as angiogenesis, cell migration, cell differentiation, and ischemia.

Interstitial fluid flow can markedly impact extracellular gradients of solutes, enhance transport of nutrients and waste, and significantly impact the development of both lymphatic and blood capillaries[4-6]. These recent studies, as well as others including our group[7-9], highlight the ability to generate living microvessels in 3-D, and also demonstrate that these living microvessels can become functional upon implantation. However, perfusion of human (or other animal) microvessels in-vitro has not been demonstrated.

In short, there have been no reports describing successful creation of actual living microvessels that are perfused with an appropriate fluid to deliver nutrients to a 3-D tissue.

BRIEF SUMMARY OF THE INVENTION

We have solved some of the above problems by mimicking the in-vivo formation of microvessels using a microfabricated platform combined with living cells and an extracellular matrix. Prior attempts have microfabricated channels in a variety of substrates (collagen, PDMS) and then coated these channels with endothelial cells. Hence, the resulting channels are not true microvessels and do not mimic the dynamics of microvessel function.

The potential impact of creating an in-vitro microtissue perfused with living microvessels can be encompassed in the broad areas of oncogenesis, ischemia, arterio-venous malformations, wound healing, drug delivery, and tissue growth, differentiation, and death. For example, the growth and development of tumors is a 3-D process that requires recruitment of host vessels for delivery of nutrients and metastasis of cells. All major modes of pharmacotherapy (e.g., oral, subcutaneous, intravenous, intramuscular) involve uptake and delivery of the drug by the circulatory system including the microcirculation. Capillary permeability and high-throughput screening of drugs are major areas of investigation that could be addressed by our proposed system. Finally, the "decision" by a tissue following insult to revitalize or undergo programmed death is poorly understood, yet is fundamental for our success in advancing human health, and must depend on a functional (i.e., perfused) capillary bed.

The general invention describes a method for creating a metabolically active microtissue that receives nutrients and eliminates waste products through a living microvessel network. As such, the long-term survival (e.g., weeks to months) of the microtissue depends on flow of fluid through the microvessels. The process describes a method for creating a direct fluidic connection between living microvessels within the device and microfluidic channels (A-V "arterio-venous" channels) within the device allowing flow of fluid between the microfluidic channels and the microvessels. The microvessels are within the metabolically active tissue, and can thus be perfused to deliver nutrients and remove waste products by convection in addition to diffusion.

Templates for the microfluidic device may comprise of materials known to those of skill in the microfabrication, such as, but not limited to PDMS, glass and/or other polymer materials.

Standard methods are used to etch or mold such micro fluidic channels into these templated materials.

Between paired A-V (arterio and venous) microfluidic channels and connected to each by a small port is a chamber/channel in which the microtissue(s) resides (i.e. the microtissue resides in the microtissue chamber). The newly developed living microvessels, growing within the microtissue, are able to deliver fluid from said microfluidic channels, through the ports, and into said microtissues growing within the microtissue chamber. This fluid (e.g., blood, cell culture media) contains nutrients, known to those of skill in the art, capable of sustaining and stimulating the tissue cells/channels. Said fluid may also contain stimulants and reagents to test the response of the microtissue/microvessel construct, e.g., toxins, drugs, circulating tumor cells.

In one embodiment, endothelial cells line the microfluidic channels and a process for creating the microtissue perfused with living microvessels is provided wherein said microvessels sprout from the endothelial cells inside said microfluidic channels in response to a stimulus from within the microtissues.

In another embodiment, cells are placed within the microtissue compartment and a process for creating the microtissue perfused with living microvessels is provided wherein said microvessels form spontaneously from the endothelial cells inside said microtissue in response to a stimulus from within the microtissues.

In another embodiment of the second preceding paragraph, the cells that can be grown in the microtissue compartment include, but not limited to, stem, endothelial, stromal, epithelial, neuronal, connective, myocardial, hepato, renal, tumor, and patient-specific cells. Such cells are hereinafter referred as "microtissue."

The stimulus for new microvessel growth can be something added (e.g., vascular endothelial growth factor, VEGF) either to the microtissue, microfluidic channels, ports, or a combination thereof, or can be derived from the cells grown in the microtissue chamber. For example, as cancer cells grow within the microtissue compartment they will exhaust the nutrient/oxygen supply and will, in response, produce signals (e.g., VEGF) that will recruit new microvessels from the outer endothelial cell-lined microfluidic channels. This is analogous to how new vessel growth works physiologically. Accordingly, this produces new microvessels.

Pressure and flow within the microfluidic channels and within the microtissue can be carefully controlled within the device to mimic physiologic and disease-related process.

In one embodiment, a process for creating a 3D metabolically active network of living microvessels is provided, comprising preparing a template comprising a plurality of microfluidic and microtissue channels, and providing a stimulus to said microfluidic channels, whereby the stimulus creates a 3D metabolically active network of living microvessels.

In an embodiment of the immediately preceding paragraph, the microvessels connect the microfluidic and microtissue channels and deliver fluid between said channels and/or the microvessels are formed within the microtissue.

In an embodiment of the second preceding paragraph, the microfluidic and microtissue channels comprise normal or diseased/abnormal cells. In yet another embodiment, these cells are selected from a group consisting of stem, endothelial, stromal, epithelial, neuronal, connective, myocardial, hepato, renal, tumor heart, liver, pancreas, muscle, brain, and kidney cells.

In an embodiment of the third preceding paragraph, the cells are obtained from an human individual.

In another embodiment, an article is provided comprising a supportive structure, one or more microfluidic channels, one or more microtissue compartments, and one or more microvessels, wherein the microvessels connect said microfluidic channels and microtissue and perfuse said microtissue, thereby allowing delivery of fluid or nutrients from the microfluidic channels to the microtissues.

In an embodiment of the immediately preceding paragraph, the microvessels are metabolically active or living and/or the microfluidic channels, microtissue or the combination thereof, is seeded with cells obtained from an individual.

In yet another embodiment, a method of identifying a candidate drug or treatment regime is provided comprising adding a test compound into a microfluidic channel within a microfluidic device, wherein the microfluidic device comprises one or more microfluidic channels, one or more microtissue compartments, and one or more microvessels, and monitoring for beneficial changes—appropriate for the drug type screened—in the microvessels, or microtissue, or a combination thereof; or the compound's kinetics.

In an embodiment of the immediately preceding paragraph, the compound is selected from a group consisting of cancer drug, cell proliferation drug, and wound healing/repair drug.

In an embodiment of the second preceding paragraph, the microfluidic channels, microtissue or the combination thereof, is seeded with cells obtained from an individual

BRIEF DESCRIPTION OF THE DRAWINGS

FIG. 3 A shows a cut-away view of microtissue compartment highlighting the communication ports that will allow sprouting microvessels to penetrate the microtissue from either arteriole or venule microfluidic channels, as well as the porous lower parylene layer for lymph drainage.

FIG. 3 B shows a top view highlighting microfluidic channels and communication ports FIG. 3 C shows venule and arteriole microfluidic channels coated with collagen (I or IV) or fibronectin, seeded with endothelial cells (black dashes) which sprout into the microfluidic channels as microvessel through the ports to deliver nutrients to the metabolizing microtissue (stromal cells in fibrin matrix).

FIGS. 8 A, 8 B and 8C shows embodiments in which the resistance to fluid flow in the microfluidic channels and the interstitial flow (flow through the tissue but not through the microvessels) through the microtissues can be manipulated to be predominantly longitudinal (panels A, B) or lateral (panel C).

DETAILED DESCRIPTION OF THE INVENTION

The term "microvessels" or "living microvessels" as used herein include arterioles, capillaries, venules, and lymphatics vessels. These living microvessels produced by the various embodiments connect the microfluidic channels to the microtissue. These microvessels are formed within the "pores" structures/channels located within the microfluidic channels (see below). They are metabolically active.

The term "microfluidic channels" as used here refer to the disclosed "arteriole" or "venuole" supplying channels, with respect to supplying or removing material from the microtissue compartment. "Arterioles" supply nutrients/fluid etc. to the microtissue; whilst "Venuoles" remove nutrients/fluid from the microtissue. These microfluidic channels are created by microfabrication technology and are not considered "3-D metabolically active" or living vessels. (i.e., the above microvessels).

The term "microtissue compartment" as used here refers to a location where cells are grown. This term includes embodiments where microtissues are grown in channels rather than in closed and isolated compartments.

The term "stimulus" refers to a condition that can be induced both mechanically (interstitial flow and pressure) or chemically (e.g., growth factors (e.g., VEGF), pH, or hypoxia) or any combination thereof, which is applied to the microfluidic channel (or cells thereof). The stimulus can also be generated/produced by the cells within the microfluidic channels themselves or from the microtissue channels (and cells thereof).

The term "fluid" as used herein refers to a liquid that is able to flow. The liquid can be blood, saline, buffer, culture media or any other solvent or media, whether the liquid is native or artificially produced.

The ability of the microvessels and microfluidic channels to be able to deliver fluid can be assessed using various methods known to those of skill in the art, including but not limited to, imaging fluorescent molecules (e.g., different molecular weight fluorescent dextrans) or fluorescent microcarrier beads (diameter less than the diameter of the pore and microvessel) that have been initially placed in the microfluidic channel.

The term "normal" in the context of "normal cells" refers to cells that are considered disease free, whether they are obtained from disease-free or asymptomatic human individuals or animals.

The term "diseased" or "abnormal" in the context of "diseased/abnormal cells" refers to cells obtained from human individuals or animals who suffer from an illness or disease known to those of skill in the art. These diseases include, but are not limited to cancers, infectious diseases, bacterial diseases, neuropathy, cardiovascular disease, nephropathy, inflammatory diseases (inflammatory bowel disease (including Crohn's disease and ulcerative colitis), asthma, dermatitis, arthritis, myasthenia gravis, Grave's disease, multiple sclerosis, and psoriasis), neurological diseases (Alzheimer's, . . . )

The term "Drug" as used herein refers to any known compound or composition, or a combination thereof, that is used to treat any disease (as referred to above). Such drugs are well known to those of skill in the art. The term also refers to compounds or compositions which are considered candidate "drugs."

Our approach to create a 3-D perfused human microvessel bed combines 3-D cell culture and microfabrication technology, and includes not only the flexibility for high-throughput design drug screening for therapeutics and toxicity, but also real-time monitoring. The overall strategy is biology-directed and inspired by the in-vivo steps of angiogenesis and vasculogenesis. A minimal architecture (i.e., matrix, angiogenic stimuli) is supplied, and the endothelial cells are allowed to create a network of microvessels to meet metabolic needs. In brief, human endothelial cells are allowed to form a microvessel network within a microtissue in response to normal or pathologic angiogenic stimuli. The angiogenic stimuli initially may be some added growth factors in the fluid in the A-V (arteriole-venule) microfluidic channels, but eventually the cells in the microtissue chamber may produce the angiogenic growth factors/stimuli. In another embodiment, the stimuli may be present simultaneously in the A-V microfluidic channels and microtissue chamber. In yet another embodiment, the stimuli may only be present in the microtissue chamber. The microtissue chamber is a closed and controlled environment, in which nutrients and waste only enter and exit from a controlled number of openings (ports) in the adjacent fluid-filled A-V channels. The flow of fluid is initially through the interstitial space, but as the microvessel network forms, the flow of fluid can divert to the living microvessels that are formed between the microfluidic and microtissue and within the microtissue itself. In yet another embodiment, the stimuli could be added to the ports.

Thus, the angiogenic stimuli are biologically-induced, and can be both mechanical (interstitial flow and pressure) and chemical (e.g., VEGF, pH, or hypoxia) in nature. The microtissue compartment is comprised of either fibrin, type I collagen, or other biomimetic matrix (synthetic or naturally occurring) as well as a human stromal cell (e.g., fibroblast, mesenchymal stem cell), which is necessary for sustained lumen formation, and, in our application, for facilitating a metabolic deficit. Other cells that could be used in the microtissue compartment, include but are not limited to, cardiac, liver, pancreas, connective tissue, nervous tissue, and muscle. In certain embodiments, the cells may comprise of tumor cells, and more particularly, tumor cells or other cells derived specifically from individual subjects i.e. patient specific tumor cells. In yet another embodiment, cardiomyocytes from human induced pluripotent stem cells (h-iPS) or cells derived from other stem cells or the stem cells themselves can be used to seed the stroma/tissue chambers. In another embodiment, another type of normal or diseased cells, obtained from an individual or patient, could be used in the microtissue compartment. A person of skill would appreciate that any combination of the aforementioned cells could also be used. Such cell types, and conditions to culture them, are known to those of skill in the art.

In one embodiment, a physiological pressure gradient within the microtissue compartment can be provided to initially induce limited nutrient fluid flow through the microtissue. As the microvessels sprout out from the microfluidic channels and grow towards the angiogenic stimulus, they eventually meet, anastomose, and deliver nutrients to the metabolizing microtissue. In short, our system mimics in-vivo angiogenesis and vasculogenesis. Additional details on the cells, matrix, and microfabrication are discussed below.

The flow and pressure within the microfluidic channels and microtissue environments can be carefully controlled within physiologic and pathological ranges by manipulating either the inlet or outlet pressures and/or the design of the microfluidic network. Such manipulation of flow pressures can also be used as a stimulus to the microfluidic channel cells to produce the microvessels.

In one embodiment, the new microvessels are with formed within the microtissue and then connect to the microfluidic channels. In an alternative embodiment, the newly formed microvessels grow/sprout from the microfluidic channels, grow into the microtissue and connect with the microvessels that are growing in from the other side. In yet another embodiment, a combination of both of the former two microvessel growth paths can occur.

Different cell types can be used to seed/coat the "arteriole" and "venule" microfluidic channels, and the "microtissue" chamber. Various cell types (endothelial cells and stromal cells) can be utilized, with the goal of maximizing design flexibility. For instance, human endothelial cells can be seeded with a stromal cell in the microtissue chamber and microvessels can spontaneously form mimicking vasculogenesis. Alternatively, the microtissue chamber can be seeded with only stromal or other tissue specific cells (e.g., cardiac) and microvessel can grow in from the "arteriole" and "venule" microfluidic channels, thus mimicking angiogenesis. The endothelial cells used to form the microvessels, which can be used to seed either the microfluidic channels, the microtissue compartment, and/or both, could come from a variety of sources including, but not limited to, human umbilical vein, aortic artery, microvasculature, or peripheral (or umbilical cord) blood-derived endothelial precursor cells. Stromal cells can also be used to help develop a stable in-vitro perfused microvascular network, and both fibroblasts and mesenchymal stem cells have been demonstrated to be effective. We have utilized both primary lung and dermal fibroblasts, as well as fibroblast cell lines. In certain embodiments, the 'venule' and "arteriole' microfluidic channels can be coated with the same endothelial cell type. In other embodiments, the 'venule' and "arteriole' channels can be coated with cells known to be derived from venule or arteriole cells, or differentiated to express those phenotypes. Such cells are cultured under conditions well known to those of skill in the art.

In one embodiment, the microfluidic device as disclosed can be used to identify candidate drugs for instance, but not limited to drugs that invoke cell death (e.g., cancer cell death), or promote cell proliferation and extracellular matrix production (e.g., wound healing). Here, cancer cells could be seeded in the microtissue channel either prior or after a microvessel network is established. The device or set up is amenable to anti-cancer drug screening through the introduction of potential drug candidates within either the microfluidic channels and/or microtissue at any particular stage of the microvessel network development process. The investigators would then be able monitor whether there was a 'beneficial' effect on either the microvessels and/or microtissues. In another embodiment, the device allows for personalized analysis by allowing cells derived from specific healthy and/or diseased individuals to be seeded into the microtissue channel and/or microfluidic channel.

The term 'beneficial' as used in this application in the context of 'beneficial effect' of a cancer drug means a desired effect on either the microvessels or microtissues as deemed appropriate to those of skill in the art, which can include but is not limited to, a reduction in growth rate; reduction in overall mass of the cancerous cells; an increase in number of normal versus abnormal cells or microvessels within the microtissue; apoptosis of the cells; a change in the function of the cells; or any combination thereof.

In another embodiment, the effect of chemical toxins or candidate toxins on the microcirculation can be determined using the disclosed device by delivering the toxin via the microfluidic channels and allowing the toxin to enter through formed microvessels or diffuse into the microtissue. Either the permeability of the chemical toxins across the microvessels or its direct toxicity on the microvessel network can be monitored or assessed. Microvessel or microtissue toxicity can be determined by conventional methods known to those of skill in the art, including the use of chemical assays; bioassays, radioactive and imaging techniques.

In another embodiment, the most effective concentration of any particular drug could be determined by the disclosed device by monitoring the response of the microvessels, microtissue or both to the drug's beneficial effects. The test compound would be delivered to the microtissue by diffusing from the microvessels or across the microtissue. The rate of delivery of the compound, and thus the optimum concentration within the microtissue depends on the desired response (i.e., increase or decrease in vessel network, cell proliferation or cell death, vessel robustness)

In another embodiment, the ability of a candidate drug that promotes cell proliferation or extra cellular matrix production or wound healing can be determined using the disclosed device. Here, The 'beneficial effect' with regards to this type of drug is on either the microvessels or microtissues—as deemed appropriate to those of skill in the art—but which can include, but is not limited to an increase in growth rate; increase microvessel network area; a change in the function of the cells; or any combination thereof.

In another embodiment, the drug kinetics could be determined by monitoring its kinetics i.e. diffusion rate from the microfluidic channels or microvessels into the microtissue.

Matrix Proteins: Collagen (type I or type IV), gelatin, fibronectin and/or fibrin can be used to coat the arteriole and venular channels, with or without the aforementioned endothelial cell types. In the microtissue compartment, both collagen (type I) and fibrin have been used to successfully support the development of in-vitro microvessels networks (i.e. the channels) as they represent the dominant extracellular matrix protein in healing wounds and connective tissue. Other natural and synthetic matrices could be employed, such as but not limited to, functionalized polyethylene glycol (PEG)

Materials to be used for the supportive structure/primary substrate layer for the microfabricated mold include, but are not limited to, glass and Si-wafers.

Materials used for the photoresist sacrificial layer are known to those of skill in the fabrication arts, whether they are positive or negative photoresist layers, or a combination thereof. These include, but are not limited to, SU-8.

Materials used for porous lower membrane to mimic the lymph drainage include, but are not limited to, Parylene. There are a number of derivatives and isomers of parylene including: Parylene N (hydrocarbon), Parylene C (one chlorine group per repeat unit), Parylene D (two chlorine groups per repeat unit), Parylene AF-4 (generic name, aliphatic flourination 4 atoms), Parylene SF (Kisco product), Parylene HT (AF-4, SCS product), Parylene A (one amine per repeat unit, Kisco product), Parylene AM (one methylene amine group per repeat unit, Kisco product), Parylene VT-4 (generic name, fluorine atoms on the aromatic ring), Parylene CF (VT-4, Kisco product), and Parylene X (a cross-linkable version, not commercially available).

3-D Model Construction.

Figure 1:
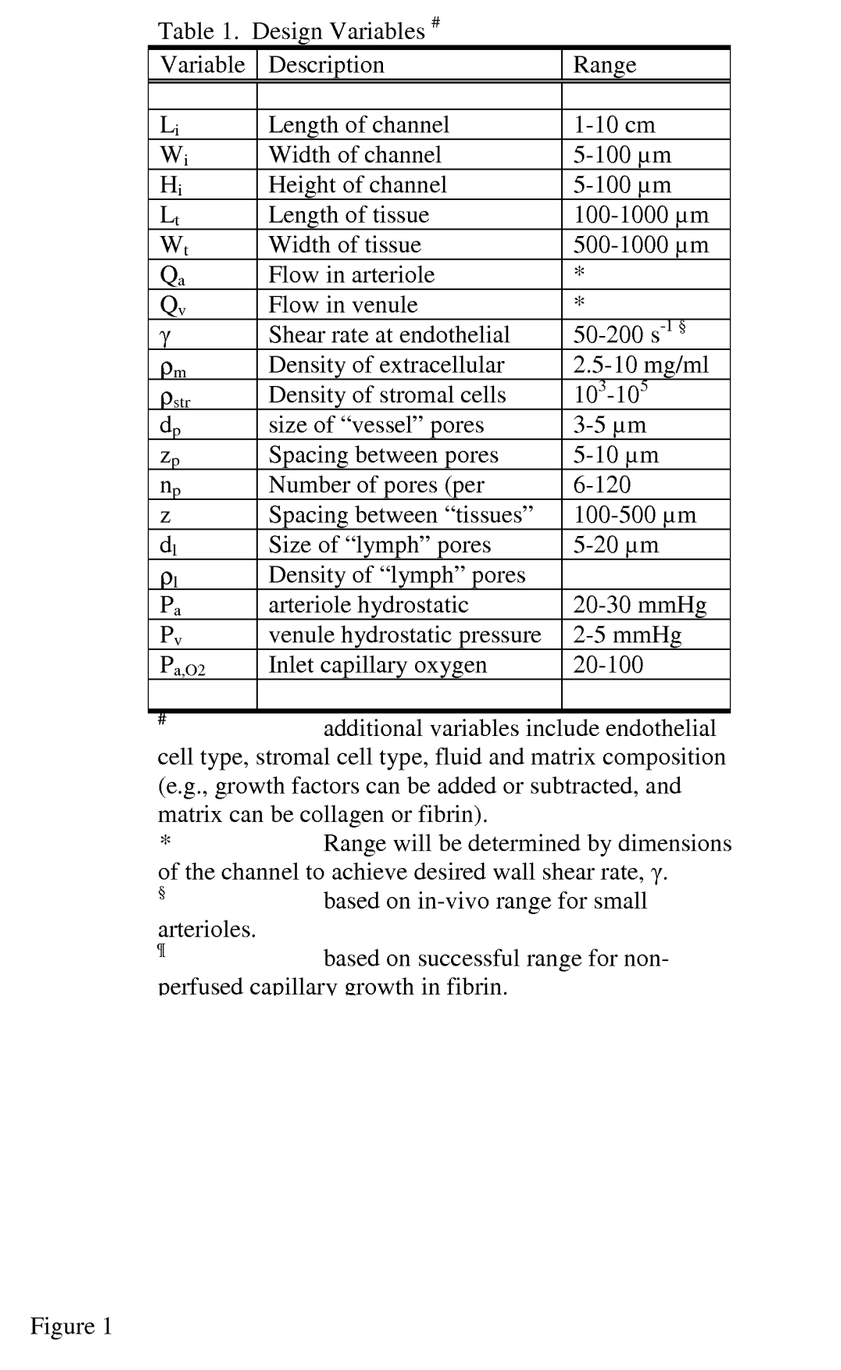
FIG. 1 presents a table showing numerous variables that affect the establishment of an in-vitro perfused microvessel bed.

The basic steps in the fabrication of the high-throughput perfused microvessel network are described in FIG. 1. The process enables a wide range of design variables (Table 1) to establish an in-vitro perfused microvessel bed. Although, particular compounds or articles have been used for such fabrication of these perfused capillary structures, such as glass slides, parylene, SU-8, and PDMS, a person of skill in the art would appreciate that any equivalent article/compounds could be used such that they are compatible with cell viability and can be used in the microfabrication process.

Figure 2:
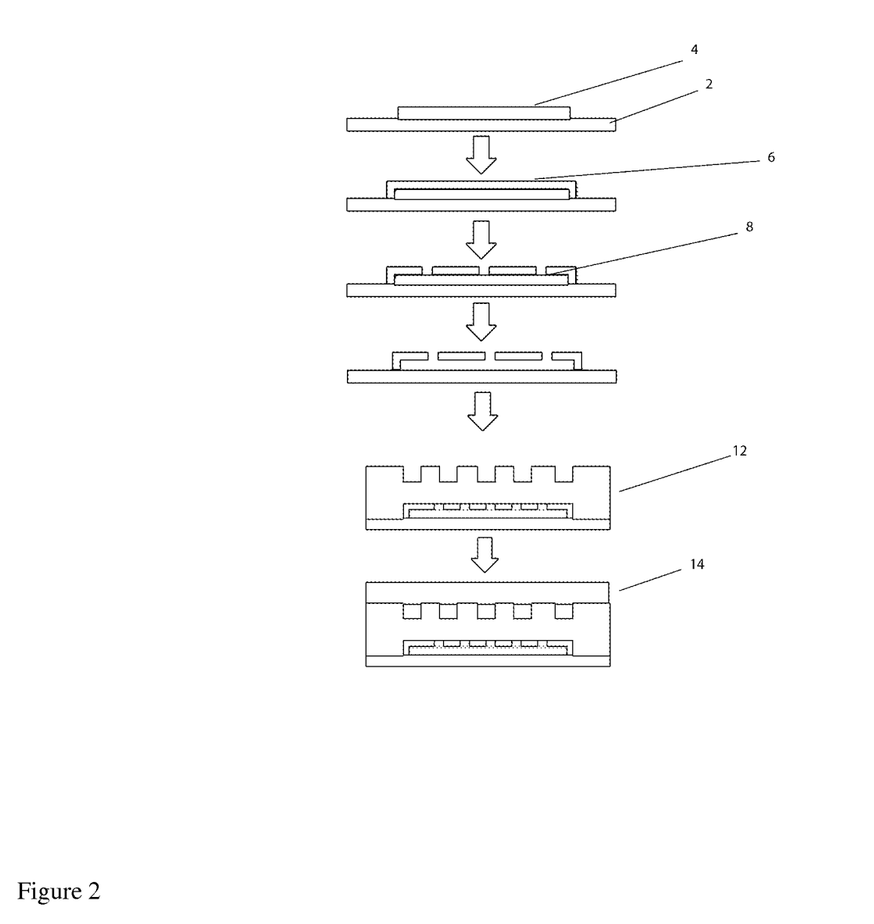
FIG. 2 shows one embodiment of a fabrication scheme for in-vitro metabolically active microtissues perfused with human microvessel bed.
Figure 3:
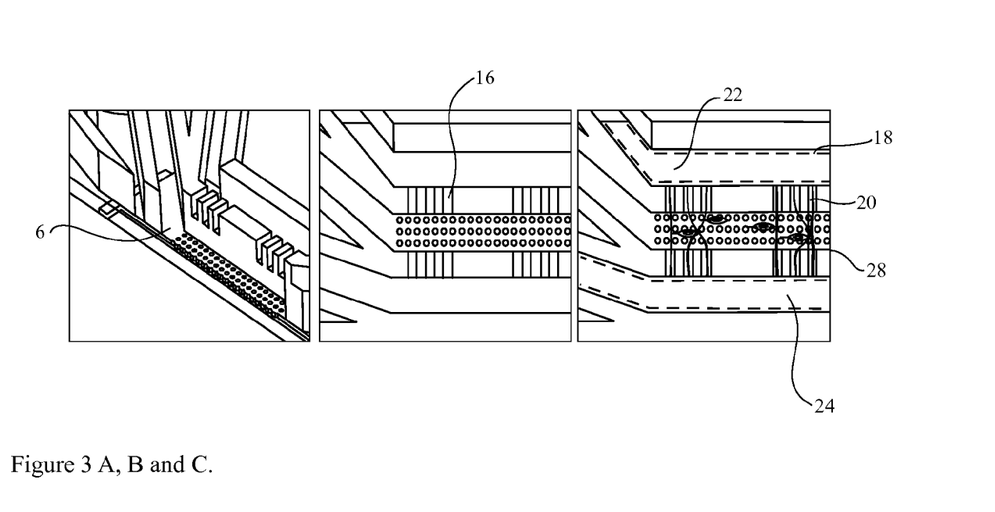

In one embodiment (not shown), for the lymph vessel drain, parylene will be vapor deposited over a photoresist sacrificial layer followed by a photolithography step to etch the holes that represent the lymph channels (FIG. 2 and FIG. 3). After the photoresist is removed, a negative resist (SU-8) will be spin coated and patterned by photolithography to establish the primary channels representing the microfluidic vessel channels (i.e. arteriole and venule). A second layer of SU-8 is then deposited to represent the arterio-venous communication ports that will sustain the capillary growth and fluid flow from arteriole to venule microfluidic channel via the microtissue in the microtissue chamber. Finally, a capping layer of polydimethyl sioloxane (PDMS) is coated with a thin layer of SU-8 and bonded with the channel structures, which can correct for any unevenness which may occur from the multiple processing steps. Since PDMS is an elastomer and compliant it can generate an excellent seal as the thin layer of SU-8 is developed and exposed to UV light (similar to the process we have previously presented)[13]. The resulting device contains a series of channels/compartments grouped in threes ("arteriole" channel, microtissue chamber, and "venule" channel) in which all physical dimensions are design variables (Table 1). Each channel/compartment can be connected to one or more reservoirs that serve as the source of fluid during the construction of the tissue and growth of the capillary network. In one embodiment, these reservoirs are illustrated as the "bulb' like structures at one or both ends of the arteriole/venule channels and microtissue chamber.

In one embodiment, following fabrication of the PDMS device, the construction of the perfused microtissues can involve the following steps. A solution of collagen IV, collagen I, or appropriate matrix protein can be used to coat the arteriole, venule, and lymph vessels channels to mimic the basement membrane. A small volume of thrombin will then be added to a solution of fibrinogen, stromal cells, and/or endothelial cells, and immediately introduced into the microtissue matrix or microtissue chamber. If collagen or other biomimetic matrix is utilized, an alternate method of "gelling" or stiffening the matrix may be required. The cellularized "tissue" then clots or polymerizes (5-10 minutes). The presence of an air-liquid interface will create surface tension at the site of the ports and inhibit flow of the solution into the arteriole, venule, or lymph vessel channels. Once coated with such matrix protein, the arteriole, venule, and lymph channels are seeded/coated with endothelial cells. Arteriole and venule fluid flow will then be introduced, and the cellularized tissue will be allowed to develop and remodel, including endothelial cell migration and microvessel formation.

Because the microtissue compartment can be a closed environment, the only source of nutrients will come from the surrounding channels/vessels. Thus, consistent with our biology-directed approach, the microtissues, for instance the stromal cells, create a metabolic deficit (hypoxic, acidic, secretion of angiogenic growth factors) and thus a pro-angiogenic environment that will induce microvessel growth from the arteriole and/or venule channels to meet metabolic demands. Such induced microvessels will grow through the communication ports between the microtissue chamber and the arteriole and/or venule channels.

FIG. 2 shows one example of a fabrication scheme for in-vitro metabolically active microtissues. Device fabrication steps include: 1) spin and pattern a sacrificial photoresist (4) onto a glass slide (2); 2) deposit parylene (6) on sacrificial photoresist; 3) etch holes in parylene (8) which will serve as drains for lymph; 4) remove sacrificial photoresist to produce floating parylene membrane; 5) spin SU-8 onto glass and parylene and photopattern the microchannels (12) for passage of nutrients and flow between the microfluidic channels and through the microtissue; 6) cover top with layer of PDMS (14) to seal device. The PDMS layer has holes for inlets and outlets.

FIG. 3 A, shows a cut-away view of microtissue channel highlighting the communication ports that will allow sprouting microvessels to penetrate tissue from either arteriole or venule channels, as well as the porous lower parylene layer (6) for lymph drainage. FIG. 3 B shows a top view highlighting channels and communication ports (16). FIG. 3C shows venule (22) and arteriole (24) channels lined with collagen (I or IV) or fibronectin, and seeded with endothelial cells (18) which sprout through the channels—as microvessels (20)—to deliver nutrients to metabolizing tissue (stromal cells 28 in fibrin matrix) via the communication pores (16).

Figure 4:
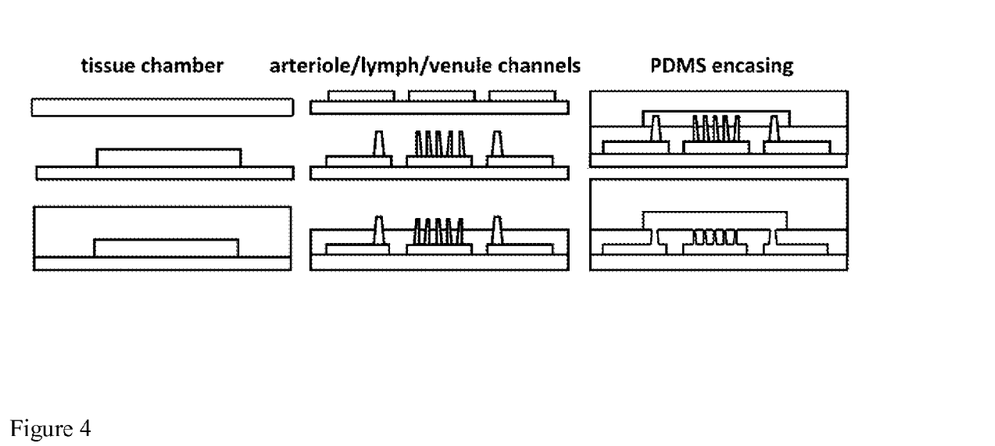
FIG. 4 shows another embodiment of a fabrication scheme for in-vitro metabolically active microtissues perfused with human microvessels.

FIG. 4 shows another example of a scheme for the fabrication of an in-vitro metabolically active microtissue. The basic steps in the fabrication of the microfluidic platform include: Standard SU-8 photolithography process will be used to fabricate two micro-molds. First, a layer of SU-8 will be spin-coated on to a Si-wafer (RCA-1 cleaned and 2% HF treated). Then, a single mask photolithography step will pattern the tissue chamber. A similar SU-8 process will also be used to create molds for arteriole, lymph, and venule channels on another Si-wafer. The ports between the microtissue chamber and microfluidic channels will be created by spin-coating a second thick layer of SU-8 on the first layer. The porous bottom layer of the lymph channels is also created by this layer of SU-8 with controlled diameter. The second mask is then used to align and pattern high aspect ratio posts for creating ports and porous bottom layer. A 3 mm thick layer of PDMS will be molded on the SU-8 mold to create the microtissue chamber. A thin layer of PDMS will also be spun on the SU-8 molds for the arteriole, lymph, and venule channels and ports. The PDMS microtissue chamber is then de-molded and bonded to the spun PDMS thin film by using O2 plasma. The bonded multilayered PDMS device is then de-molded and holes punched to create inlet/outlet to each channel (microtissue and microfluidic) before bonding to another 1 mm thick PDMS plate to seal channels. The main difference in this design scheme compared to that in FIG. 2 is the placement of the microtissue chamber on a different plane (at a different height). This allows the endothelial cells to develop over a flat surface in the fluidic channels and avoids sharp curvatures that appeared to limit cell attachment.

Figure 5A:
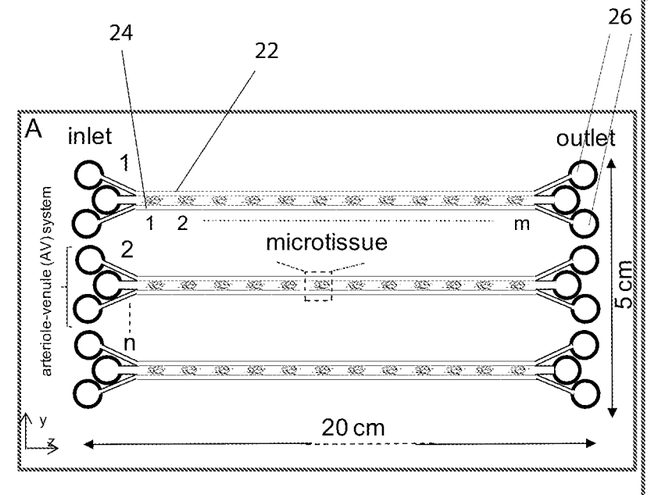
FIG. 5a shows one example of a fabrication scheme/arrangement for high throughput in-vitro perfused human microvessels.
Figure 5B:
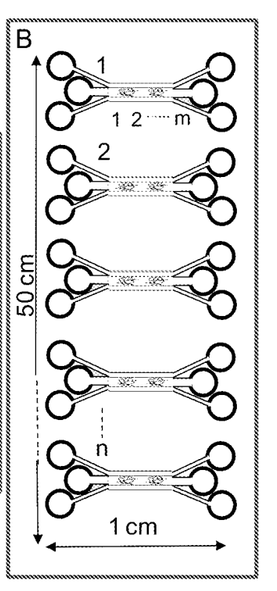
FIG. 5b shows a second example a fabrication scheme/arrangement for high throughput in-vitro perfused human microvessels.
Figure 6:
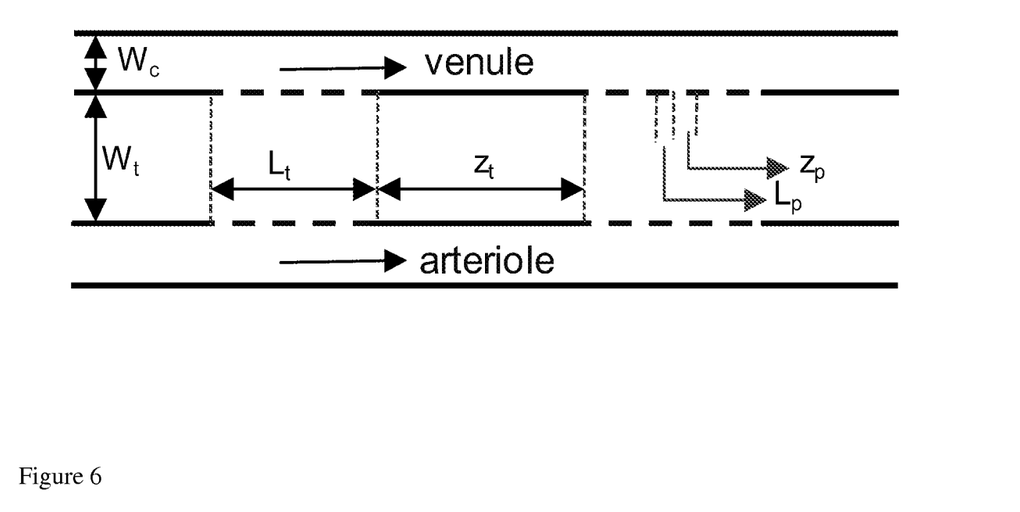
FIG. 6 shows some dimensions which define the A-V system connected by the microtissues.

FIGS. 5A and B show other embodiments for multiple design options for high-throughput are available including FIG. 5A) a relatively small (n=10) number of long (20 cm) arteriole-venule (A-V) systems on a single platform. In this design, significant gradients in diffusible species along the z-direction would develop. This would be useful to investigate a large range of concentration of soluble species (e.g., oxygen, VEGF). In one embodiment, each A-V system (including reservoirs 26) will span approximately 5 mm in the y-direction. In addition, if the length of each microtissue compartment was 500 μm (Lt, Table 1) and the separation distance between microtissue was also 500 μm (zt, Table 1), each microtissue compartment would contain approximately m=200 microtissues. Thus, this platform could investigate the function of 2000 (m×n) similar or different types of microtissues. FIG. 5B) An alternative design representing a relatively large number (n=50) of much shorter (1 cm) A-V systems. This design would minimize spatial gradients in the z-direction and provide a greater number of observations of microtissues which are exposed to the feed (inlet) conditions (i.e., concentration at z=0). In this case there would be approximately m=10 microtissues along each A-V system in the z-direction, and 100 AV systems in the y-direction, or 1000 (m×n) microtissues on a single platform. In FIGS. 5A and 5B, the venules are shown as 22, and arterioles as 24.

Figure 8:
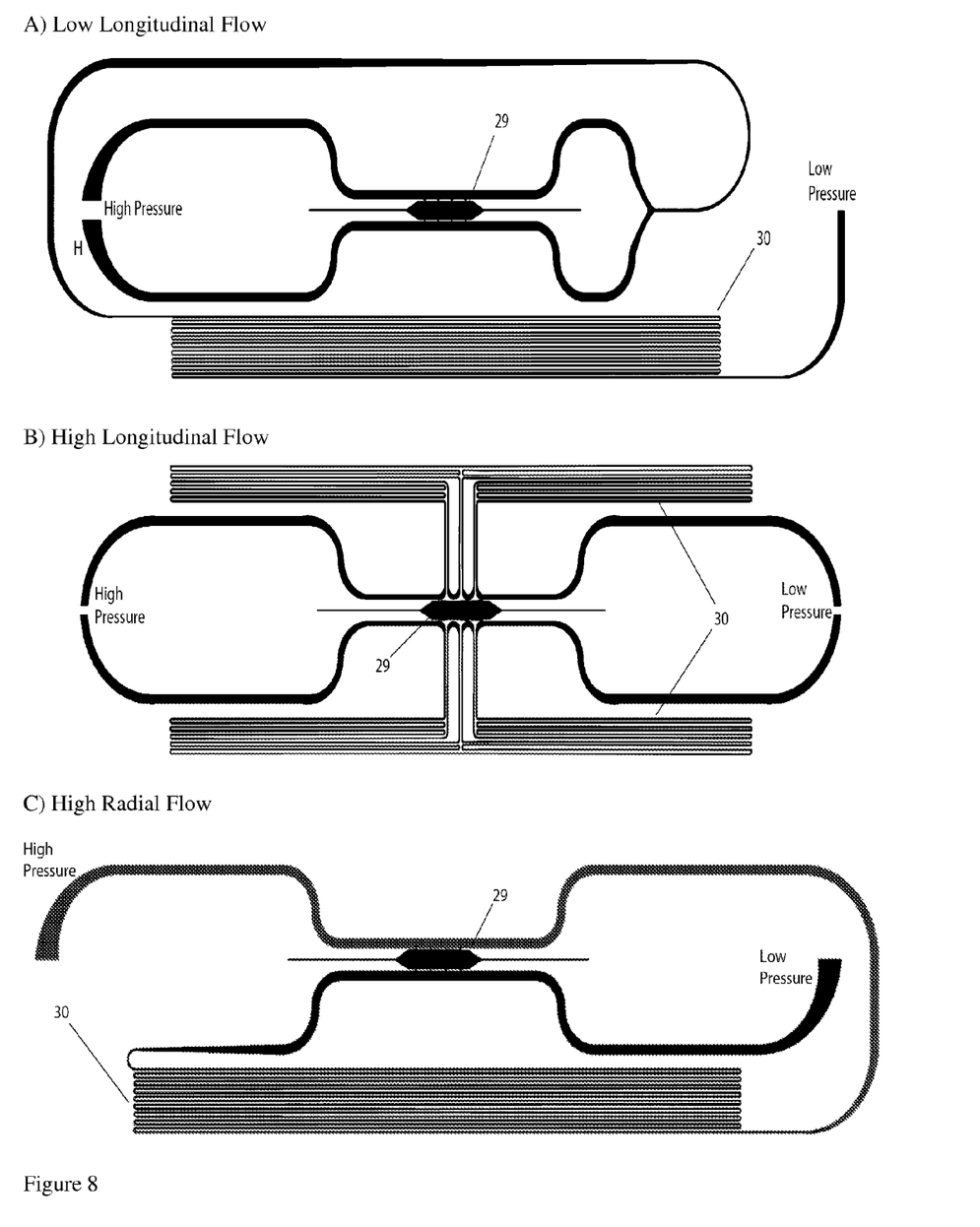

Further examples include methods to control the pressure and flow in the microtissues (29). FIG. 8 includes a method by which long serpentine fluidic channels (30) can be strategically placed such that the pressure gradient is nearly constant across the individual microtissues (radial direction, z-axis), (8A, B) but significant along the microtissues (longitudinal direction, y-axis) (8B) or vice versa (8C).

The microfluidic device was fabricated by standard polydimethlsiloxane micro-molding. The device consists of 2 fluid-filled microfluidic channels (arteriole and venule) on either side of a central metabolically active microtissue chamber consisting of normal human fibroblasts seeded ($2 \times 10^6$ cells/ml) in a fibrin matrix. For the study of angiogenesis-like processes, human endothelial progenitor cell-derived endothelial cells (ECs) were used to line ($1 \times 10^6$ cells/ml) the fluid-filled side channels (arteriole and venules) and allowed to migrate into and grow within the microtissue chamber via communicating ports (see FIG. 3). To simulate vasculogenic-like processes, in some devices ECs were randomly distributed throughout the microtissue chamber with the fibroblasts. A pressure gradient (2 mm $H_2O$) across the tissue chamber was applied once obvious network formation was identified. Flow in formed microvessels was assessed by adding 1 μm diameter polystyrene fluorescent beads into the microfluidic channels and tracking their movement in the formed microvesels across the tissue chamber. Multiphoton microscopy was used to image devices stained for CD31 markers (EC marker) and DAPI (nuclei stain).

In one embodiment, the three microfabricated compartments (arteriole channel, tissue chamber, and venule channel) can be formed so that all three are on the same horizontal level. In yet another embodiment, the arteriole and venule channels can be formed so that they are both at different levels to the tissue chamber, for instance, these channels are formed above the level of the microtissue chamber. In yet another embodiment, the arteriole and venule channels are not only at different level from the microtissue chamber but also on different levels from each other.

Figure 7:
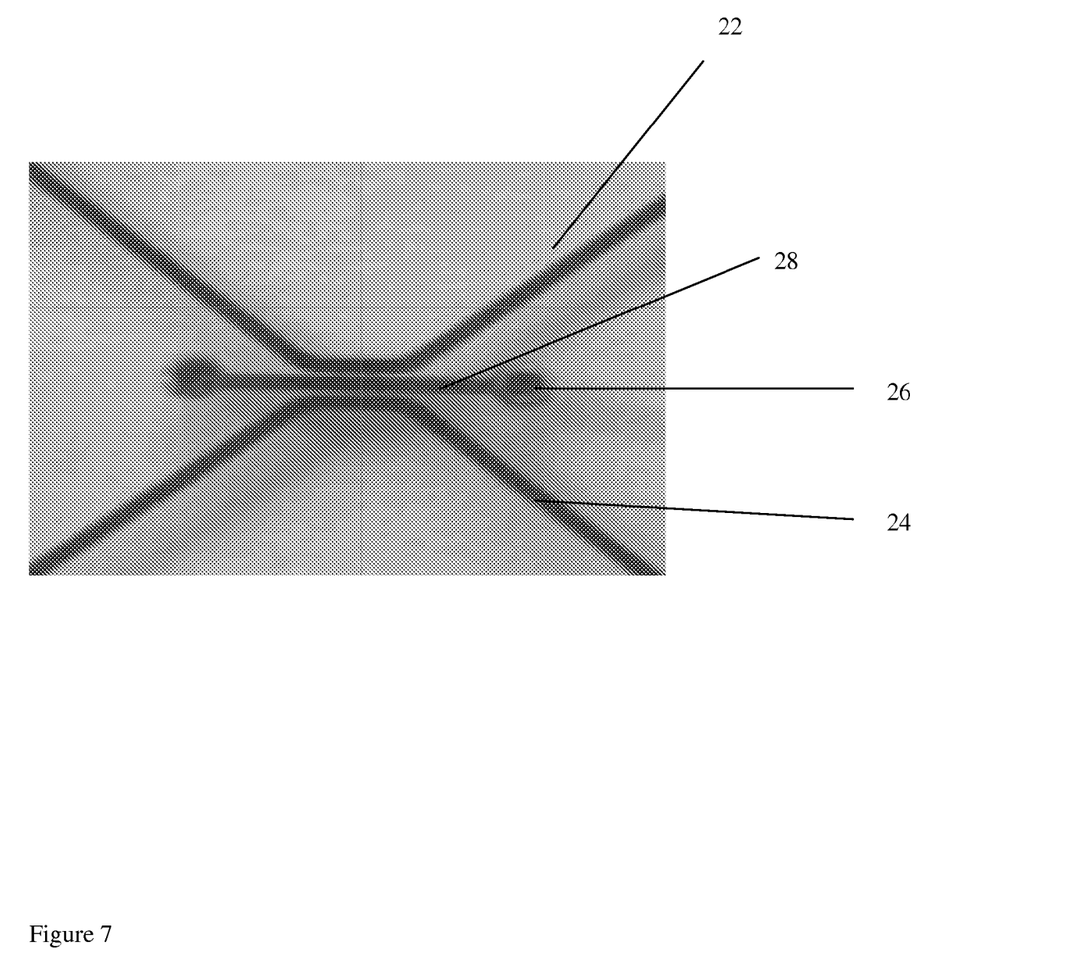
FIG. 7 shows another embodiment of a fabrication arrangement.

In one embodiment, the arteriole and venule channels do not have to run parallel throughout their entire lengths to the microtissue chamber. FIG. 7 shows a view of such a fabricated 3D cell system as viewed under a microscope. Here, only a small region of the venule channel (22) and arteriole channel (24) is shown running parallel to the microtissue chamber (28). Also shown are the reservoirs (26) for the microtissue chamber (reservoirs for the venules and arterioles are not depicted on this figure).

Figure 9:
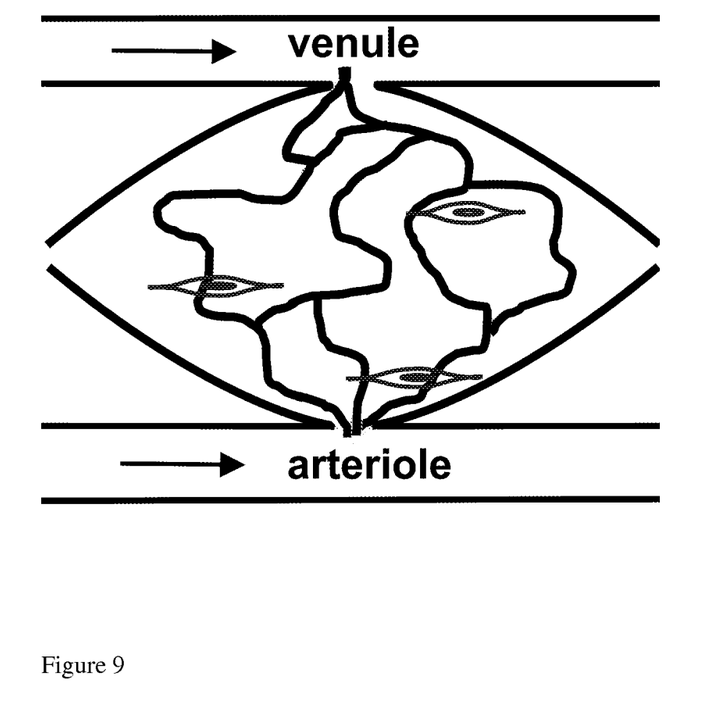
FIG. 9 shows another embodiment in which the microtissue "channel" is shaped like a diamond to provide separation (diffusion and/or convection) of this tissue from neighboring tissues.

In yet another embodiment, the microtissue chamber can be alternate shapes (e.g., diamonds or tear-drops) rather than one long central microtissue channel/chamber (FIG. 9). This design facilitates the separation of the tissues by diffusion, although the microvessels may (but are not required to) still penetrate between the microtissue compartments for a fluidic connection.

Results

Cells in the device remain viable under flow conditions through 40 days. For the device simulating angiogenesis, vacuoles consistent with early lumen formation were observed within a week of culture. When both endothelial cells and stromal cells are cultured in the microtissue chamber early perfusion of a partially formed vessel network was confirmed at 3 weeks and monitored through 40 days. Tracking microbeads introduced into the venule-like microfluidic channels reveal flow speed estimates of 35-200 μm/s. At day 40, 20 μl/day of fluid flow across the microtissue was recorded. Staining and imaging analysis confirmed the formation of tubules with lumens. (data not shown).

REFERENCES (WHICH ARE ALL INCORPORATED BY REFERENCE IN THEIR ENTIRETY)

1. Barenstein J, Teraj H, King K, Weinberg E, Kaazempur-Mofrad M, and Vacanti J. Microfabrication technology for vascularized tissue engineering. Biomed Microdevices 4: 167-175, 2002.
2. Shin M, Matsuda K, Ishii O, Terai H, Kaazempur-Mofrad M, Borenstein J, Detmar M, and Vacanti J P. Endothelialized networks with a vascular geometry in microfabricated poly(dimethyl siloxane). Biomed Microdevices 6: 269-278, 2004.
3. Chrobak K M, Potter D R, and Tien J. Formation of perfused, functional microvascular tubes in vitro. Microvasc Res 71: 185-196, 2006.
4. Helm C L, Fleury M E, Zisch A H, Boschetti F, and Swartz M A. Synergy between interstitial flow and VEGF directs capillary morphogenesis in vitro through a gradient amplification mechanism. Proc Natl Acad Sci USA 102: 15779-15784, 2005.
5. Helm C L, Zisch A, and Swartz M A. Engineered blood and lymphatic capillaries in 3-D VEGF-fibrin-collagen matrices with interstitial flow. Biotechnol Bioeng 96: 167-176, 2007.
6. Ng C P, Helm C L, and Swartz M A. Interstitial flow differentially stimulates blood and lymphatic endothelial cell morphogenesis in vitro. Microvasc Res 68: 258-264, 2004.
7. Chen X, Aledia A S, Ghajar C M, Griffith C K, Putnam A J, Hughes C W C, and George S C. Prevascularizing an engineered tissue construct accelerates formation of functional anastomosis with host vasculature. Tissue Eng (in press) 2008.
8. Ghajar C M, Chen X, Harris J W, Suresh V, Hughes C C, Jeon N L, Putnam A J, and George S C. The effect of matrix density on the regulation of 3-D capillary morphogenesis. Biophys J 94: 1930-1941, 2008.
9. Griffith C K, Miller C, Sainson R C, Calvert J W, Jeon N L, Hughes C C, and George S C. Diffusion limits of an in vitro thick prevascularized tissue. Tissue Eng 11: 257-266, 2005.

The invention claimed is:
1. A three-dimensional cell system, comprising:
a plurality of microfabricated microfluidic channels including a first microfabricated microfluidic channel and a second microfabricated microfluidic channel formed within a non-biological supportive material;
one or more microfabricated compartments formed within the non-biological supportive material;
cells combined with a biomimetic matrix and residing in at least one microfabricated compartment of the one or more microfabricated compartments; and
one or more living microvessels formed subsequent to placement of the cells combined with the biomimetic matrix within the at least one microfabricated compartment, wherein the one or more living microvessels including a first living microvessel that connects to the first microfabricated microfluidic channel and the sec- ond microfabricated microfluidic channel, the first living microvessel having a lumen and running from the first microfabricated microfluidic channel, through the at least one microfabricated compartment, and to the second microfabricated microfluidic channel, and the one or more living microvessels perfusing the cells combined with the biomimetic matrix and coupling together the plurality of microfabricated microfluidic channels, wherein the one or more living microvessels allow for (i) delivery of nutrients from a fluid flowing from the first microfabricated microfluidic channel of the plurality of microfabricated microfluidic channels to the cells combined with the biomimetic matrix and (ii) removal of at least waste products from the fluid flowing to the second microfabricated microfluidic channel of the plurality of microfabricated microfluidic channels, wherein the fluid flows inside the lumen of the one or more living microvessels, and wherein the one or more living microvessels are selected from a group consisting of (i) one or more living lymphatic vessels and (ii) one or more living blood vessels.

2. The three-dimensional cell system of claim 1, wherein the plurality of microfabricated microfluidic channels, or a combination of the plurality of microfabricated microfluidic channels and the cells combined with the biomimetic matrix, is seeded with cells obtained from an individual.

3. The three-dimensional cell system of claim 1, wherein the plurality of microfabricated microfluidic channels comprise seeded endothelial cells, seeded stromal cells, or both the seeded endothelial cells and the seeded stromal cells.

4. The three-dimensional cell system of claim 1, wherein the cells combined with the biomimetic matrix comprise human cells, cancer cells, or patient-specific cells.

5. The three-dimensional cell system of claim 4, wherein the human cells comprise normal or diseased cells selected from a group consisting of stem cells, endothelial cells, stromal cells, epithelial cells, neuronal cells, connective cells, myocardial cells, hepatocytes, renal, heart cells, liver cells, pancreatic cells, muscle cells, brain cells, kidney cells, tumor cells, and patient-specific cells.

6. The three-dimensional cell system of claim 1, wherein the first living microvessel allows for delivery of the nutrients within the fluid that provides viability of the cells combined with the biomimetic matrix.

7. The three-dimensional cell system of claim 1, wherein the fluid includes nutrients, and further includes a stimulant, a reagent, or a combination thereof, for testing a response of one or more of the cells combined with the biomimetic matrix.

8. The three-dimensional cell system of claim 7, wherein the fluid includes a drug that corresponds to the stimulant, the reagent, or the combination of the stimulant and the reagent.

9. The three-dimensional cell system of claim 1, wherein survival of the cells combined with the biomimetic matrix depends, at least in part, on movement of the fluid through the first living microvessel.

10. The three-dimensional cell system of claim 1, wherein the one or more living microvessels sprout from endothelial cells inside the plurality of microfabricated microfluidic channels in response to a stimulus from within the cells combined with the biomimetic matrix.

11. The three-dimensional cell system of claim 1, wherein the one or more living microvessels sprout from endothelial cells inside the cells combined with the biomimetic matrix in response to a stimulus from within the cells combined with the biomimetic matrix.

12. The three-dimensional cell system of claim 1, wherein the one or more living microvessels sprout from endothelial cells inside the cells combined with the biomimetic matrix in response to a stimulus, the stimulus being a condition induced by mechanical, chemical or a combination of mechanical and chemical factors.

13. The three-dimensional cell system of claim 1, wherein the one or more living microvessels are formed in response to a stimulus, the stimulus being based, at least in part, on a controlled pressure within at least one of the plurality of microfabricated microfluidic channels.

14. The three-dimensional cell system of claim 1, wherein the one or more living microvessels are formed in response to a stimulus, the stimulus being based, at least in part, on a controlled pressure within the at least one microfabricated compartment.

15. The three-dimensional cell system of claim 1, wherein the one or more living microvessels comprises a microvessel network including a plurality of interconnected living microvessels.

16. The three-dimensional cell system of claim 1, wherein the supportive material comprises polydimethyl siloxane (PDMS).

17. The three-dimensional cell system of claim 1, wherein the one or more living microvessels include a second living microvessel that connects to the first and second microfabricated microfluidic channels.

18. The three-dimensional cell system of claim 1, wherein the one or more living microvessels are the one or more living blood vessels.

19. The three-dimensional cell system of claim 18, wherein the one or more living blood vessels are metabolically active.

20. The three-dimensional cell system of claim 18, wherein the one or more living blood vessels comprise endothelial cells derived from endothelial cells seeding the plurality of microfabricated microfluidic channels.

21. The three-dimensional cell system of claim 18, wherein the one or more living blood vessels comprise endothelial cells derived from the cells combined with the biomimetic matrix.

22. The three-dimensional cell system of claim 18, wherein the one or more living blood vessels form developing blood vessel networks.

23. The three-dimensional cell system of claim 18, wherein the one or more living blood vessels are capable of sprouting additional blood vessels.

24. The three-dimensional cell system of claim 18, wherein the one or more living blood vessels are stimulated to form in response to fluid flow rate in the plurality of microfabricated microfluidic channels.

25. The three-dimensional cell system of claim 1, wherein the one or more living microvessels are the one or more living lymphatic vessels.

* * * * *